US00PP32766P2

(12) United States Plant Patent
Olesen

(10) Patent No.: US PP32,766 P2
(45) Date of Patent: Jan. 26, 2021

(54) COMPACT FLORIBUNDA ROSE PLANT NAMED 'POULPAL083'

(50) Latin Name: ***Rosa* hybrid**
Varietal Denomination: Poulpal083

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,266

(22) Filed: Sep. 3, 2019

(51) Int. Cl.
*A01H 5/02* (2018.01)
*A01H 6/74* (2018.01)

(52) U.S. Cl.
USPC ..... Plt./143

(58) Field of Classification Search
USPC ..... Plt./101, 141, 143
See application file for complete search history.

(56) References Cited

PUBLICATIONS

Poulsen Roser. 2020. (http://www.poulsenroser.com/assortment/rose-collections/palace/eltham.aspx). 2 pages. (Year: 2020).*

* cited by examiner

*Primary Examiner* — Susan McCormick Ewoldt
*Assistant Examiner* — Karen M Redden

(57) ABSTRACT

A new garden rose plant of the Compact Floribunda class which has abundant, pink and white striped flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal083'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal083', originated as a single seedling from the stated cross.

The new variety may be distinguished from its male pollen parent and female seed parent primarily by the following characteristics. The male pollen parent plant has ivory white flowers while the new variety has pink and white striped flowers. The female seed parent plant has solid pink flowers while the new variety has pink and white striped flowers.

The objective of the hybridization of this rose variety was to create a new and distinct variety with unique qualities, such as:

1. Uniform and abundant pink and white striped flowers;
2. Vigorous, but compact growth when propagated on its own roots;
3. Exceptional disease resistance.

This combination of qualities is not present in previously available commercial cultivars of this type, known to the inventor, and distinguish 'Poulpal083' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal083' was selected in the spring of 2012 by the inventor as a single plant from the progeny of the aforementioned hybridization.

Asexual reproduction of 'Poulpal083' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal083' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal083'.

Specifically illustrated in FIG. 1 of the drawings are a cluster of open flowers on a branch.

Figure 1:
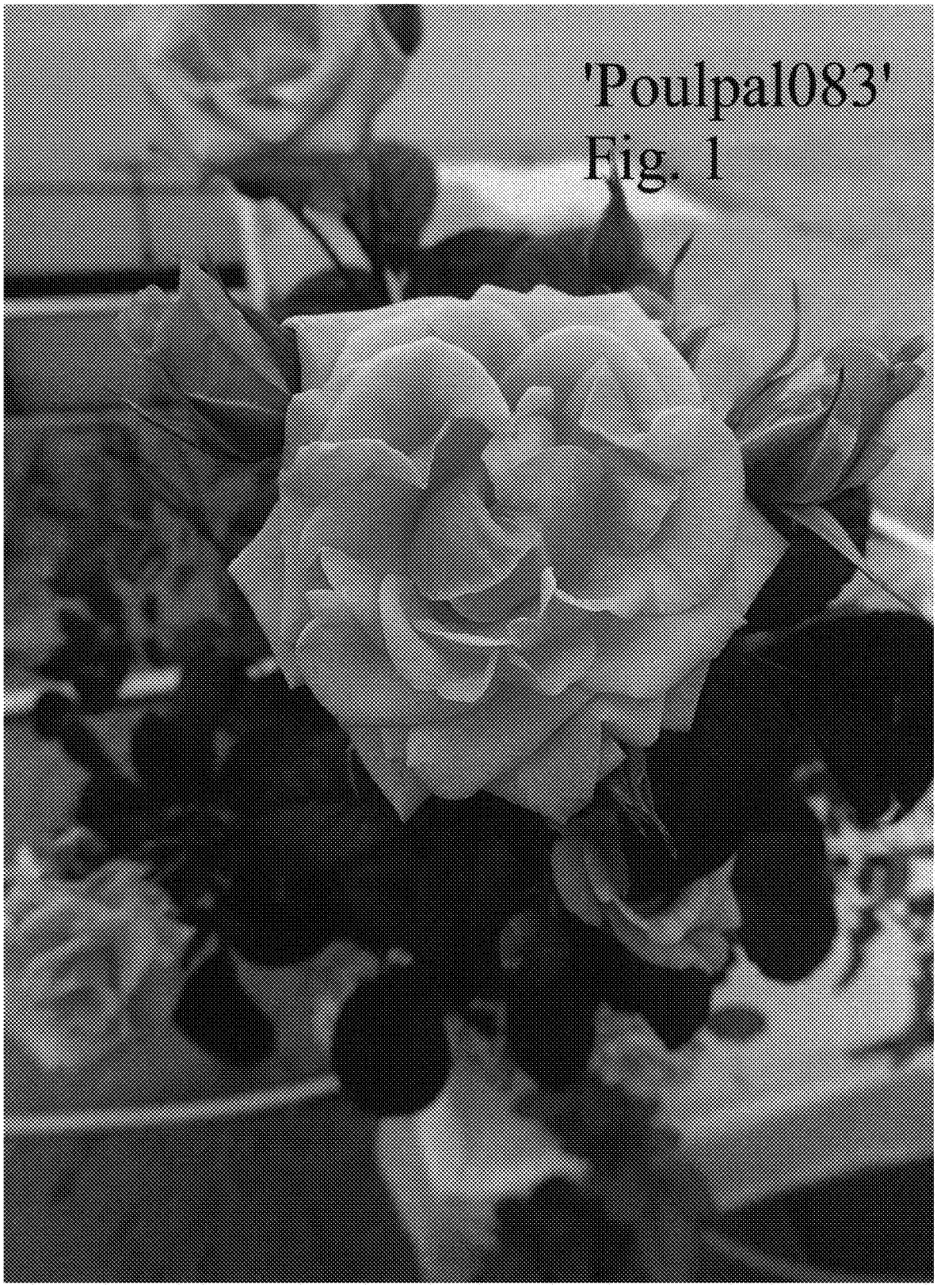
Figure 2:
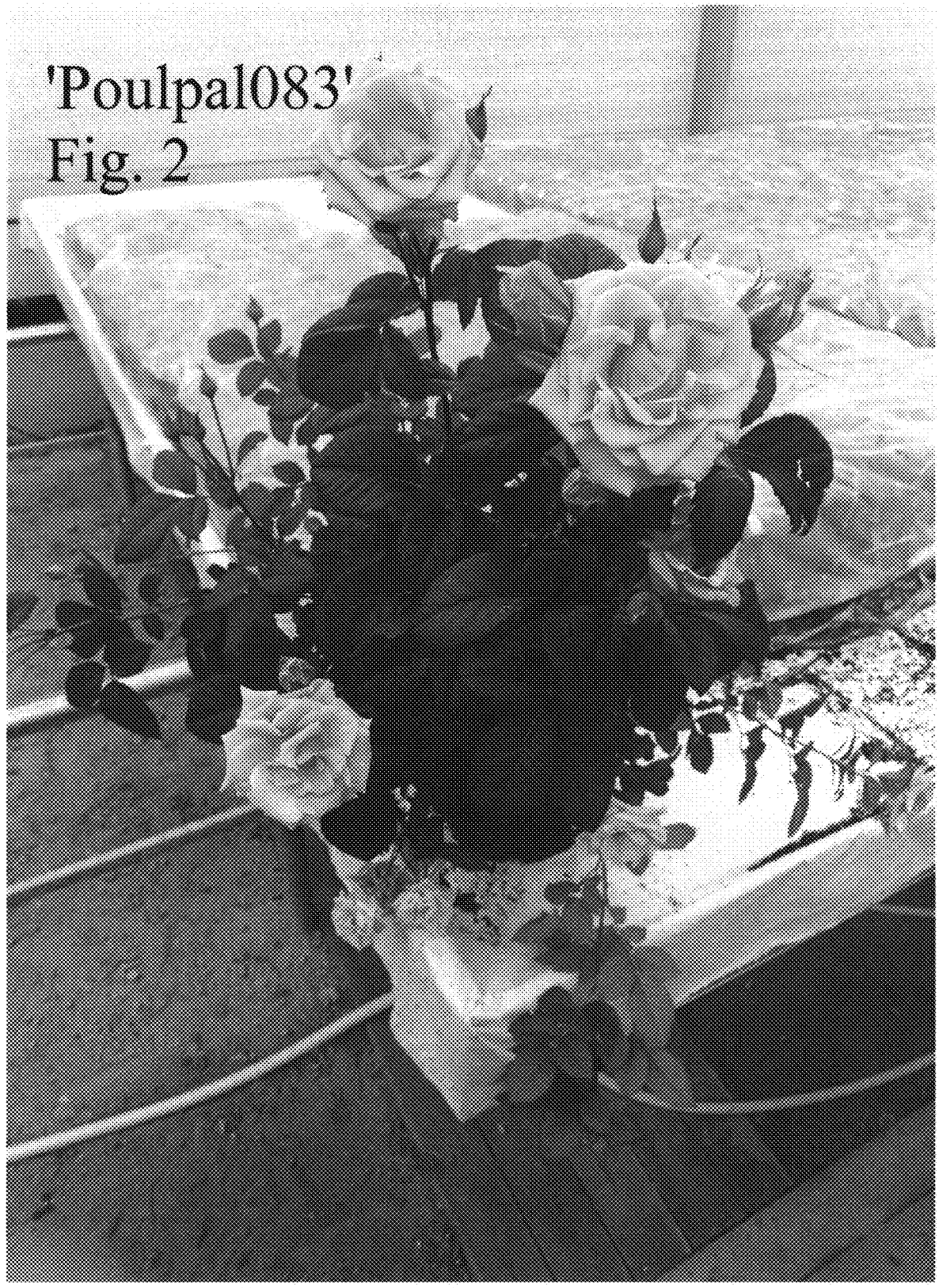

Specifically illustrated in FIG. 2 of the drawings is the entire plant in flower. Plants shown are 1 year of age.

DETAILED DESCRIPTION OF THE VARIETY

The following is a description of 'Poulpal083', as observed in its growth in a container nursery in Odense Denmark. Observed plants are 1 year of age, and were grown on their own roots. Color references are made using The Royal Horticultural Society (London, England) Colour Chart, 2001, except where common terms of color are used.

For a comparison, several physical characteristics of the rose variety 'Poulpah068', U.S. Plant Pat. No. 25,970 are compared to 'Poulpal083' in Chart 1.

CHART 1

| | 'Poulpal083' | 'Poulpah068' |
|---|---|---|
| Petal Count | 35 petals | 20 petals |
| Flower Diameter | 60 to 70 mm | 75 mm |
| General Tonality of Flower Color | Red Group 55B | Red Group 52A with intonations of Red Group 43D. Splashed with White Group N155B |

FLOWER AND FLOWER BUD

Blooming habit: Continuous.

Flower bud:

*Size.*—Upon opening, 25 mm in length from base of receptacle to end of bud. Bud diameter is 14 mm.

*Bud form.*—Ovate.

*Bud color.*—As sepals divide petals are Red-Purple Group 58B.

*Sepal inner surface.*—Color: Green Group 138B. Surface: Smooth and pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—23 mm long by 9 mm wide.

*Receptacle.*—Texture: Smooth. Size: 10 mm in height by 7 mm wide. Color: Yellow-Green Group 144A. Shape: Campanulate.

*Pedicel.*—Surface: Smooth. Length: 25 to 35 mm. Diameter: 2 mm on average. Color: Yellow-Green Group 144B. Strength: Strong.

*Peduncle.*—Length: 20 to 50 mm. Diameter: 3 mm. Color: Yellow-Green Group 144A.

Flower bud development: Flower buds are borne in clusters of about 3 flower buds per stem.

Flower bloom:

*Fragrance.*—Moderate to strong perfume.

*Duration.*—The blooms have a duration on the plant of approximately 14 days. Petals fall cleanly away from plant after flowers have fully matured.

*Size.*—Flower diameter is 60 to 70 mm when open. Flower depth is 30 mm.

*Flower shape.*—General shape is a rosette with overlapping petals of different sizes.

*Shape of flower, side view.*—The upper portion is flat. The lower portion is convex.

Petalage: Under normal conditions, flowers have 35 petals total, 5 to 7 of which are petaloids.

General tonality of flower: Open flowers are Red Group 55B.

Petal color:

*Upon opening, outer and inner petals.*—Upper surface: Red Group 55B streaked with Red Group 56D. Lower surface: Red-Purple Group 58D.

*After opening, outer and inner petals.*—Upper surface: Red Group 55B streaked with Red Group 56D. Lower surface: Red-Purple Group 58D.

Petals:

*Petal reflex.*—Somewhat reflexed.

*Margin.*—Entire and uniform. Moderate undulations of margin observed.

*Shape.*—Broad elliptic. Apex shape: Rounded. Base shape: Acute.

*Size.*—On average 35 mm (l) 42 mm (w).

*Texture.*—Smooth.

*Thickness.*—Average.

Petaloids:

*Size.*—20 mm (l) by 10 mm (w).

*Quantity.*—5 to 7.

*Shape.*—Elliptic, with an acute base and round apex.

*Color.*—Same as petals.

Reproductive organs:

*Pollen.*—None observed.

*Anthers.*—Size: 2 mm in length. Color: Greyed-Yellow Group 162B. Quantity: 38 on average.

*Filaments.*—Color: Yellow Group 13B. Length: 4 mm.

*Pistils.*—Length: 3 mm. Quantity: 22 on average.

*Stigmas.*—Color: Greyed-Yellow Group 160C.

*Styles.*—Color: Green-White Group 157A.

*Hips.*—None Observed.

PLANT

Plant growth: Upright. Plants are 40 cm in height, and 35 cm wide.

Stems:

*Color.*—Juvenile growth: Yellow-Green Group 144A. Mature growth: Yellow-Green Group 146B.

*Length.*—On average, canes are 15 to 20 cm from the base of the plant to the flowering portion.

*Diameter.*—5 mm.

*Internodes.*—On mature canes, there is an average distance of 40 mm between nodes.

*Surface texture.*—Young wood: Smooth. Older wood: Smooth.

Long prickles: None observed.

Plant foliage:

*Compound leaf.*—115 mm (l)×68 (w).

*Quantity.*—2 leaves per 10 cm of stem on average.

*Color of juvenile foliage.*—Upper side: Yellow-Green Group 147A. Lower side: Yellow-Green Group 147B.

*Color of mature foliage.*—Upper side: Yellow-Green Group 147A. Lower side: Yellow-Green Group 147B.

Plant leaves and leaflets:

*Stipules.*—Size: 15 mm in length. Quantity: 2 per compound leaf. Shape: Linear, slightly broad based with outward extending apices. Margins: Finely serrated. Color: Yellow-Green Group 144A.

*Petiole.*—Length: 20 mm. Diameter: 1 mm.

*Upper surface.*—Color: Yellow-Green Group 144A.

*Lower surface.*—Color: Yellow-Green Group 144B.

*Rachis.*—Length: 40 mm. Upper surface: Color: Yellow-Green Group 144A.

*Lower surface.*—Color: Yellow-Green Group 144B. Observations: Small prickles.

*Leaflet.*—Quantity: Normal number of leaflets leaves in middle of the stem is 5 leaflets. Margins: Serrated.

Size: Average size of the terminal leaflet on normal leaves is 45 mm in length by 32 mm wide. Shape: Generally ovate. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal083', substantially as illustrated and described herein, due to its abundant pink and white striped flowers, disease resistance, and extended period of bloom.

* * * * *

'Poulpal083'

'Poulpal083'